(12) United States Patent
Nichols et al.

(10) Patent No.: US 9,294,802 B1
(45) Date of Patent: Mar. 22, 2016

(54) GESTURE CONTROL BASED ON PROSTHETIC NERVE SIGNAL DETECTION

(71) Applicant: Rovi Guides, Inc., Santa Clara, CA (US)

(72) Inventors: Michael R. Nichols, Cambridge, MA (US); Danielle Larson, Santa Monica, CA (US)

(73) Assignee: Rovi Guides, Inc., Santa Clara, CA (US)

( * ) Notice: Subject to any disclaimer, the term of this patent is extended or adjusted under 35 U.S.C. 154(b) by 0 days.

(21) Appl. No.: 14/609,749

(22) Filed: Jan. 30, 2015

(51) Int. Cl.
*H04N 21/422* (2011.01)
*H04N 21/482* (2011.01)
*G06F 3/01* (2006.01)

(52) U.S. Cl.
CPC .......... *H04N 21/42201* (2013.01); *G06F 3/015* (2013.01); *H04N 21/42207* (2013.01); *H04N 21/4821* (2013.01)

(58) Field of Classification Search
CPC combination set(s) only.
See application file for complete search history.

(56) References Cited

U.S. PATENT DOCUMENTS

| | | | |
|---|---|---|---|
| 6,239,794 B1 | 5/2001 | Yuen et al. | |
| 6,388,714 B1 | 5/2002 | Schein et al. | |
| 6,564,378 B1 | 5/2003 | Satterfield et al. | |
| 6,695,885 B2 | 2/2004 | Schulman et al. | |
| 6,756,997 B1 | 6/2004 | Ward, III et al. | |
| 7,165,098 B1 | 1/2007 | Boyer et al. | |
| 7,283,867 B2 | 10/2007 | Strother et al. | |
| 7,761,892 B2 | 7/2010 | Ellis et al. | |
| 7,813,809 B2 | 10/2010 | Strother et al. | |
| 8,046,801 B2 | 10/2011 | Ellis et al. | |
| 8,060,910 B2 | 11/2011 | Cruz et al. | |
| 2002/0174430 A1 | 11/2002 | Ellis et al. | |
| 2003/0110499 A1 | 6/2003 | Knudson et al. | |
| 2005/0251827 A1 | 11/2005 | Ellis et al. | |
| 2009/0326406 A1* | 12/2009 | Tan .......................... G06F 1/163 600/546 |
| 2010/0153885 A1 | 6/2010 | Yates | |
| 2012/0090003 A1* | 4/2012 | Dove ............... H04N 21/42201 725/38 |
| 2013/0265218 A1* | 10/2013 | Moscarillo .............. G06F 3/017 345/156 |
| 2014/0031952 A1 | 1/2014 | Harshbarger et al. | |
| 2014/0198035 A1* | 7/2014 | Bailey ..................... G06F 3/014 345/156 |

OTHER PUBLICATIONS

U.S. Appl. No. 14/038,158.
U.S. Appl. No. 11/179,410.
<http:/youtube/rgU3gUh3q_c> (uploaded Jan. 30, 2010).
http://www.ncbi.nlm.nih.gov/pmc/articles/PMC3157946/ (2008).
Medusa.sdsu.edu/Robotics/Neuromuscular/Theses/Sijiang/Chapter2.pdf (updated).
Sudarsan et al., "Design and Development of EMG controlled prosthetics limb," 38:3547-3551 (2012).

* cited by examiner

*Primary Examiner* — Mulugeta Mengesha
(74) *Attorney, Agent, or Firm* — Ropes & Gray LLP

(57) ABSTRACT

Methods and systems are disclosed herein for a media guidance application which may control a user device, which may receive a radio-frequency signal from a user device, corresponding to an electromyography signature received from a user. The media guidance application may also cross-reference the electromyography signature with first and second databases to determine an attempted user motion and a media guidance application operation corresponding to the electromyography signature. In response to determining the media guidance application operation to be performed, the media guidance application may perform said media guidance application operation on the user device.

18 Claims, 6 Drawing Sheets

GESTURE CONTROL BASED ON PROSTHETIC NERVE SIGNAL DETECTION

BACKGROUND OF THE INVENTION

In conventional media guidance systems, consumers access media through a media guide by interacting with a media guidance system, for example by pressing buttons on a remote, or by interacting with a touch screen. Interacting with a media guidance system with these conventional methods is prohibited and/or at least difficult for individuals such as amputees. Amputees may wear prosthetics, but these prosthetics are typically large, uncomfortable and generally ill-suited to media guide conventional operations through conventional devices such as handheld remote controls, touchscreen interfaces, etc. Accordingly, an amputee may not be able to conveniently control a media guide application. At the very least, amputees may find that even with prosthetic limbs they are unable to search and access media as easily as able-bodied individuals, significantly reducing their quality of life.

SUMMARY

Accordingly, methods and systems are disclosed herein for a media guidance application that allows amputees to more easily control media guidance systems by relieving them from having to use their prosthetic to control the media guidance system. Amputees using these methods and systems can interact with media guidance systems with the same ease and comfort as able-bodied users. A user device fitted to an amputee's remaining limb allows the amputee to control a prosthetic (when a prosthetic is worn) and/or to forgo using the prosthetic to enter traditional inputs when the prosthetic is not worn. A user device, such as one implementing a media guidance application, is configured to receive and process a signal emitted by the user device fitted to an amputee's remaining limb, where this signal encodes a user's brain activity and associated myoelectric signals, which may control either a prosthetic, or directly interact with the media guidance application system in order to navigate, recommend, provide access to, and perform operations related to media content. A user device implementing a media guidance application system as disclosed herein may more efficiently meet the needs of a user with specific needs, such as a user with an amputated limb by allowing the user to perform various functions, including, but not limited to: providing on-screen options that display or provide access to operations without the need for a user to interact with the options via conventional means, providing suggestions of user intended motions for the user to control the media guidance application through the user's EMG signature and transmitted RF signal, learning new user intended motions and corresponding media guidance application operations, and providing the user with alternate means to control the media guidance application should the RF signal representing the user intended motion not be sufficient.

In some aspects, a media guidance application (or a user device upon which the media guidance application is implemented) may receive a remote signal such as a radio-frequency (RF) signal from a user device, where the RF signal corresponds to an EMG signature received from a user. The electromyography signature ("EMG") may be created by an electromyogram unit indicating electrical activity of muscles of the user. For example, an EMG may indicate (by detecting the electrical activity of muscles associated with the movement of a phantom limb) that a user missing a limb, i.e. having a "phantom" limb, intends to move the phantom limb in a certain way. For example, a user may have an amputated hand, and may generally use a hand prosthetic, controlled by implantable myoelectric sensors ("IMES"), such that when the user intends to move the phantom hand, whether the prosthetic hand is present or absent, an EMG signature indicative of the phantom hand movement can be created and processed into a signal, e.g. an RF signal.

The media guidance application (or a user device upon which the media guidance application is implemented) may cross-reference the EMG signature resulting from a user's intended motion of a phantom limb with a first database listing EMG signatures that correspond to different attempted user motions, to determine an attempted user motion that corresponds to the user EMG signature. For example, when a user intends/attempts to move a phantom limb, e.g. a phantom hand, the unique EMG signature generated by the electrical activity of the user's muscles is cross-referenced with a database of EMG signatures to determine that the particular EMG pattern created by the user corresponds to a pattern which corresponds to movement of a hand, and/or a pattern which corresponds to a specific movement of a hand, e.g. movement of an index finger from left to right.

The media guidance application (or a user device upon which the media guidance application is implemented) may cross-reference the attempted user motion that corresponds to the user EMG signature with a second database listing media guidance application operations to determine a media guidance application operation that corresponds to the attempted user motion. For example, when a user EMG signature has been determined with the help of the first database to correspond to an intended user motion of an index from left to right, the media guidance application determines whether this intended user motion corresponds to a known media guidance application operation. For example, a movement from left to right of an index finger may be recognized as a scrolling motion, which may enable a user to scroll through channel listings or VOD offerings.

The media guidance application (or a user device upon which the media guidance application is implemented) may, in response to determining the media guidance application operation to be performed, perform this media guidance application operation on the user device. For example, the media guidance application (or a user device upon which the media guidance application is implemented) may carry out the scrolling motion and scroll through channel listings or VOD offerings, as requested by the user.

In some embodiments, a media guidance application (or a user device upon which the media guidance application is implemented) receives an RF signal by receiving an EMG signature from the user at a telemetry controller, and by processing the EMG signature at the telemetry controller into the received RF signal. For example, the telemetry controller may be located with the user, may be associated directly or indirectly with the user's prosthetic, may be integrated with the user equipment, and/or may be distinct from both the user and the user equipment.

In some embodiments, the media guidance application (or a user device upon which the media guidance application is implemented) may fail to identify a matching user motion after cross-referencing a user EMG signature with the database listing EMG signatures corresponding to different attempted user motions. In this case, the media guidance application (or a user device upon which the media guidance application is implemented) may request that the telemetry controller be recalibrated.

In some embodiments, the media guidance application (or a user device upon which the media guidance application is implemented) may fail to identify a media guidance application operation when cross-referencing a user intended motion with the database listing user intended motions corresponding to media guidance application operations. In this case, the media guidance application (or a user device upon which the media guidance application is implemented) may also request the telemetry controller be recalibrated. For example, the telemetry controller may be recalibrated when a new user is operating the user equipment, and/or when a user is operating a different phantom limb associated with a different prosthetic, or when a user is operating under different circumstances such as a different mood, or any other circumstance which may have an impact on the user's EMG signature.

In some embodiments, in response to not determining an attempted user motion corresponding to a user's EMG signature, the media guidance application (or a user device upon which the media guidance application is implemented) may prompt the user to enter the attempted user option by a different method, to allow for the database associating EMG signatures and attempted user motions to be updated. For example, a user may create an EMG signature by attempting to move their index finger from left to right. When the media guidance application (or a user device upon which the media guidance application is implemented) cannot cross-reference the EMG signature created by the user with an intended motion, either because the EMG signature is incomplete, and/or specific to the user, and/or otherwise unknown to the database, the media guidance application (or a user device upon which the media guidance application is implemented) may let a user indicate their intended motion for future use. For example, a media guidance application (or a user device upon which the media guidance application is implemented) may let a user enter their intended motion by typing, speaking, and/or using conventional user input means such as a keyboard, mouse and/or remote control.

In some embodiments, in response to not determining an attempted user motion corresponding to the user's EMG signature, a media guidance application (or a user device upon which the media guidance application is implemented) may query a source other than the cross-referencing database. For example, the media guidance application (or a user device upon which the media guidance application is implemented) may connect to a remote server including a larger database, and/or query the internet or peer devices to search for the attempted user motion.

Similarly, in some embodiments, in response to not determining the media guidance application operation that corresponds to the attempted user motion, the media guidance application (or a user device upon which the media guidance application is implemented) may search for an attempted user motion from a different source. For example, the media guidance application (or a user device upon which the media guidance application is implemented) may connect to a remote server including a larger database, and/or query the internet or peer devices to search for the attempted user motion.

In some embodiments, in response to not determining the media guidance application operation corresponding to the attempted user motion, the media guidance application (or a user device upon which the media guidance application is implemented) may also prompt a user to enter the media guidance application operation by a different method and/or different user input device, to allow the database listing attempted user motions and their corresponding media guidance application operations to be updated.

For example, in a learning mode, the media guidance application (or a user device upon which the media guidance application is implemented) may allow a user to select a command through conventional means, such as a remote control. The media guidance application (or a user device upon which the media guidance application is implemented) may then prompt the user to make a movement, to allow the attempted user motion to be associated in the database listing attempted user motions and their corresponding media guidance application operations for future use.

In some embodiments, in response to not determining the media guidance application operation that corresponds to the attempted user motion, the media guidance application (or a user device upon which the media guidance application is implemented) may generate for display to the user a media guidance application operation which resembles the attempted user motion.

For example, the media guidance application (or a user device upon which the media guidance application is implemented) may detect an EMG signature partially matching a scrolling motion, and/or detect an incomplete scrolling motion, and suggest to the user the "correct" motion, by indicating a motion, e.g. with a left to right arrow, and associated instructions, e.g. "swipe your index finger to scroll." For example, the media guidance application (or a user device upon which the media guidance application is implemented) may allow the user to correct the user input to match the suggested command, and/or if the user is unable or unwilling to correct his or her intended motion, the media guidance application (or a user device upon which the media guidance application is implemented) may allow the user to confirm that the motion suggested by the media guidance application is the motion the user intended to make.

It should be noted, the systems, methods, apparatuses, and/or aspects described above may be applied to, or used in accordance with, other systems, methods, apparatuses, and/or aspects.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which.

DETAILED DESCRIPTION OF DRAWINGS

Figure 1:
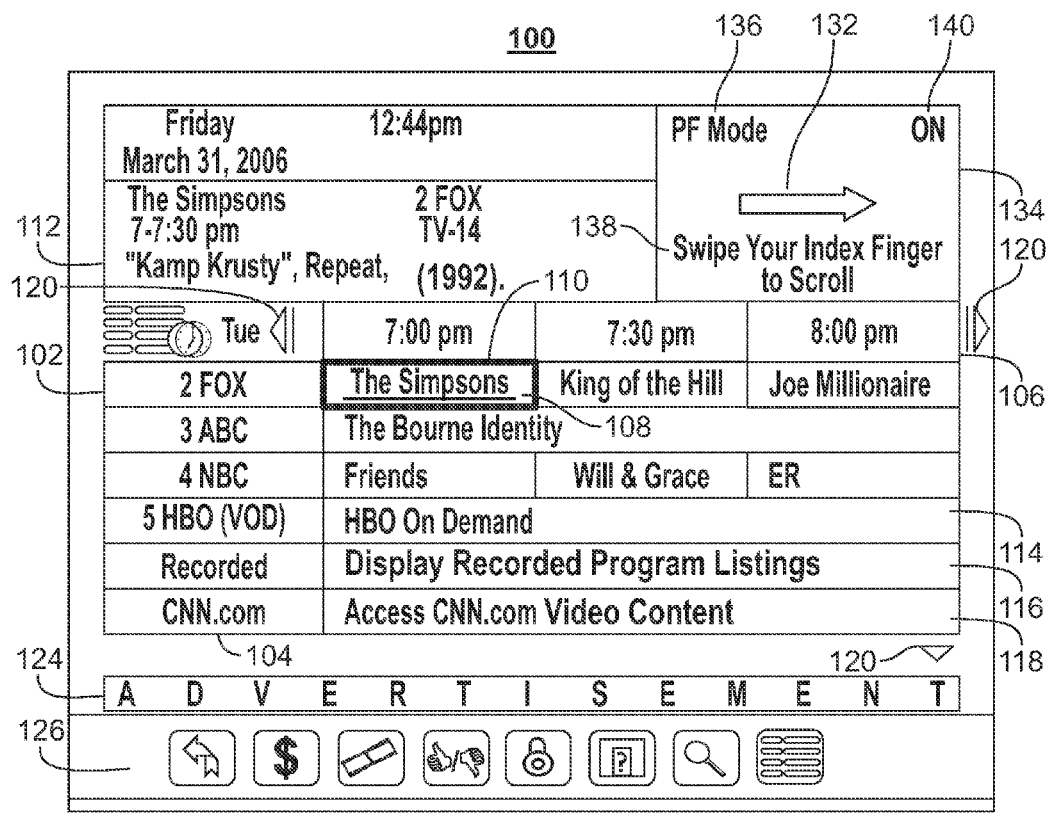
FIG. 1 shows an illustrative media guidance application for selecting media assets in accordance with some embodiments of the disclosure.

Methods and systems are disclosed herein for a media guidance application configured to perform a media guidance application operation in response to a user intended motion. The amount of content available to users in any given content delivery system can be substantial. Many users desire a form of media guidance through an interface that allows users to efficiently navigate content selections and easily identify content that they may desire. An application that provides such guidance is referred to herein as an interactive media guidance application or, sometimes, a media guidance application or a guidance application.

Interactive media guidance applications may take various forms depending on the content for which they provide guidance. One typical type of media guidance application is an interactive television program guide. Interactive television program guides (sometimes referred to as electronic program guides) are well-known guidance applications that, among other things, allow users to navigate among and locate many types of content or media assets. Interactive media guidance applications may generate graphical user interface screens that enable a user to navigate among, locate and select content. As referred to herein, the terms "media asset" and "content" should be understood to mean an electronically consumable user asset, such as television programming, as well as pay-per-view programs, on-demand programs (as in video-on-demand (VOD) systems), Internet content (e.g., streaming content, downloadable content, Webcasts, etc.), video clips, audio, content information, pictures, rotating images, documents, playlists, websites, articles, books, electronic books, blogs, advertisements, chat sessions, social media, applications, games, and/or any other media or multimedia and/or combination of the same. Guidance applications also allow users to navigate among and locate content. As referred to herein, the term "multimedia" should be understood to mean content that utilizes at least two different content forms described above, for example, text, audio, images, video, or interactivity content forms. Content may be recorded, played, displayed or accessed by user equipment devices, but can also be part of a live performance.

The media guidance application and/or any instructions for performing any of the embodiments discussed herein may be encoded on computer readable media. Computer readable media includes any media capable of storing data. The computer readable media may be transitory, including, but not limited to, propagating electrical or electromagnetic signals, or may be non-transitory including, but not limited to, volatile and non-volatile computer memory or storage devices such as a hard disk, floppy disk, USB drive, DVD, CD, media cards, register memory, processor caches, Random Access Memory ("RAM"), etc.

With the advent of the Internet, mobile computing, and high-speed wireless networks, users are accessing media on user equipment devices which they traditionally did not use. As referred to herein, the phrase "user equipment device," "user equipment," "user device," "electronic device," "electronic equipment," "media equipment device," or "media device" should be understood to mean any device for accessing the content described above, such as a television, a Smart TV, a set-top box, an integrated receiver decoder (IRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a hand-held computer, a stationary telephone, a personal digital assistant (PDA), a mobile telephone, a portable video player, a portable music player, a portable gaming machine, a smart phone, or any other television equipment, computing equipment, or wireless device, and/or combination of the same. In some embodiments, the user equipment device may have a front facing screen and a rear facing screen, multiple front screens, or multiple angled screens. In some embodiments, the user equipment device may have a front facing camera and/or a rear facing camera. On these user equipment devices, users may be able to navigate among and locate the same content available through a television. Consequently, media guidance may be available on these devices, as well. The guidance provided may be for content available only through a television, for content available only through one or more of other types of user equipment devices, or for content available both through a television and one or more of the other types of user equipment devices. The media guidance applications may be provided as on-line applications (i.e., provided on a web-site), or as stand-alone applications or clients on user equipment devices. Various devices and platforms that may implement media guidance applications are described in more detail below.

In some embodiments, a user device may be configured to receive, process and aggregate electrical signals from a user's brain into a remote signal which may be transmitted to a media guidance application (or a user device upon which the media guidance application is implemented) to control the media guidance application (or the user device upon which the media guidance application may be implemented) and to request media guidance application operations. For example, a user missing a right hand may have acquired a right-hand prosthetic. However, a prosthetic, no matter how advanced, is not a perfect replica of a user's limb in terms of mobility and sensation: a prosthetic typically provides only limited mobility, may be bulky, may be difficult to control precisely, and may feel foreign to a user. Accordingly, the user may find it cumbersome to use his or her prosthetic to operate elements of a media guidance system, such as a remote control. Instead, an amputee may wish to enjoy a sense of normalcy when operating a media guidance application, and wish to be able to interact with a media guidance system as if they had all their limbs. For example, a user may regret the days prior to amputation when they were able to scroll through program listings by moving the fingers of their missing hand in a scrolling motion. Such a user may wish to "scroll" even in their current situation, with a missing hand. Similarly, a user missing a thumb may wish to "press" the arrow keys of a remote control, as if still able to with their thumb, to switch program listings.

In some embodiments, a user may control a media guidance application (or a user device upon which the media guidance application is implemented) by intending the motions of their missing limb, such as moving their "phantom" index finger from left to right, or pressing a button with their "phantom" thumb. Intending a motion may include attempting a motion, part of a motion, thinking of a motion, and/or any combination of myoelectric signals or any brain activity which may form a unique pattern.

In some embodiments, a motion may be defined as an attempted motion, i.e. a motion which a user with a missing appendage wills the missing appendage to carry out. In some embodiments, such a motion may be detected by measuring myoelectric signals received at a sensor location. Prosthetic devices may be coupled with sensors. For example, sensors receive the electrical signals carried from the user's brain to the sensors, where the electrical signals correspond to the intended phantom limb motion.

In some embodiments, a motion may be defined as a motion imagined by the user, e.g. a motion which the user pictures in his/her mind, which may lead to associated myoelectric signals being propagated to the sensor locations, but which may also exist even in the absence of myoelectric signals being propagated from the user's brain. For example, brain activity may be measured at the user's brain, and/or the user's thoughts or moods may be monitored to detect intended or "pictured" motions.

In some embodiments, a motion may be any motion associated with the myoelectric signals measured at a sensor location, to include involuntary motions. For example, a user's unconscious reflex or random brain activity not associated with a motion of a limb may be defined as a motion.

In some embodiments, based on a user's brain activity, data may be gathered from sensors such as implantable myoelectric sensors (IMES) and aggregated into an EMG signature or pattern, which may be transmitted to the media guidance application or user device on which the media guidance application is implemented. Different types of embedded and/or implantable sensors may be used to measure electrical activity associated with a brain of a user, as transferred to muscle fibers. For example, IMES sensors may measure properties of electrical signals or fluctuations received at a location near a user's muscles, e.g. near an amputated or "phantom" limb. The coupling between an implantable stimulator/sensor and a prosthetic device is described in more detail in U.S. Pat. No. 6,695,885, and U.S. Pat. No. 7,283,867, hereby incorporated by reference herein in its entirety.

In some embodiments, the sensors, and/or the telemetry controller which may be used to aggregate and process signals from multiple sensors, may communicate with other devices through RF signals. For example, a telemetry controller may communicate with a prosthetic, or any other device configured to receive an RF signal, such as a set-top-box or any user device upon which a media guidance application is implemented. Additional discussion about the use of radio frequency antennas to communicate with a set top box apparatus, and the use of multi-modal neural interfacing for prosthetic devices is described in detail in U.S. Pat. No. 8,060,910, U.S. Patent Application Publication No. 2014/0031952, and U.S. Pat. No. 7,813,809 which are hereby incorporated by reference herein in their entirety.

The media guidance application (or a user device upon which the media guidance application is implemented) may operate in a plurality of modes each associated with sensitivity levels. The media guidance application may determine that a particular mode corresponds to determining a user, whether a different mode corresponds to determining patterns for a specific user.

For example, the media guidance application may store settings associated with specific devices or users. For example, the brain wave patterns of a first user may have overall amplitude or frequencies which differ significantly from those of another user. Alternatively, the brain wave patterns associated with movement of a phantom finger may differ significantly from the brain wave patterns, e.g. EMG signature, associated with a phantom arm.

Furthermore, the media guidance application may automatically adjust the various modes initiated and/or switch from one mode to another. For example, in response to detecting a new user associated with a different IEMS device, the media guidance application may change from a first mode to a second mode. In one such example, a first user with a left hand prosthetic may be interacting with a media guidance application. A second user with a different prosthetic may then wish to interact with the media guidance application. The media guidance application may detect a change in user, and change modes accordingly. Alternatively, in response to detecting a new user, the media guidance application may initiate a recalibration of the telemetry controller.

In some embodiments, a user may turn on or off a mode which allows users to control the media guidance application through their sensors. For example, this control mode may be referred to as a prosthetic-free of "PF" mode. A user may turn on the "PF" mode of the media guidance application system, and interact with the media guidance system either with their prosthetic worn and connected to their body, or with prosthetic disconnected from their body. For example, while in PF mode, a user may still prefer to use their prosthetic when hosting guests. Alternatively, also in the "PF" mode a user may choose to relax and rest their limb supporting the prosthetic. In some embodiments, in order for the media guidance application system to communicate with the user through the PF mode, the user's device, e.g. IMES device, may be turned on.

In some embodiments, the users may need to learn how to communicate with the media guidance application (or user device upon which the media guidance application is implemented) before the interaction becomes second nature. For example, a "PF" learning mode may be selected by the user, or be automatically selected by the media guidance application. In PF learning mode, the media guidance application may provide on-screen feedback about the information received via the RF signal, to allow the user to learn how to communicate more instructions, and/or more accurate instructions through their intended motions.

In some embodiments, the user device receiving RF signals from the users may also require "conventional" instruction from the user to improve the interaction between the user and the user device. For example, the media guidance application (or user device upon which the media guidance application is implemented) may not recognize a user intended motion or a user intended operation, and may prompt the user to enter the intended motion or media guidance application operation through alternate means, such as through a remote, keyboard, mouse, voice recognition, facial recognition, or any other method.

The method and systems described herein may be applied to a vast array of social and scientific fields such as advertising, personal or commercial entertainment, and/or medical therapy. Amputees may be able to control any device capable of receiving an RF signal by intending motions, and/or transmitting myoelectric signals forming characteristic EEG signatures. For example, an amputee may control a cell phone to text, email, or browse by intending motions such as pressing keys on the cell phone device. In another example, an amputee may control and interact with an in-home system such as a surveillance system or temperature system.

One of the operations of the media guidance application is to provide media guidance data to users. As referred to herein, the phrase, "media guidance data" or "guidance data" should be understood to mean any data related to content or data used in operating the guidance application. For example, the guidance data may include program information, guidance application settings, user preferences, user profile information, media listings, media-related information (e.g., broadcast times, broadcast channels, titles, descriptions, ratings information (e.g., parental control ratings, critic's ratings, etc.), genre or category information, actor information, logo data for broadcasters' or providers' logos, etc.), media format (e.g., standard definition, high definition, 3D, etc.), advertisement information (e.g., text, images, media clips, etc.), on-demand information, blogs, websites, and any other type of guidance data that is helpful for a user to navigate among and locate desired content selections.

Figure 2:
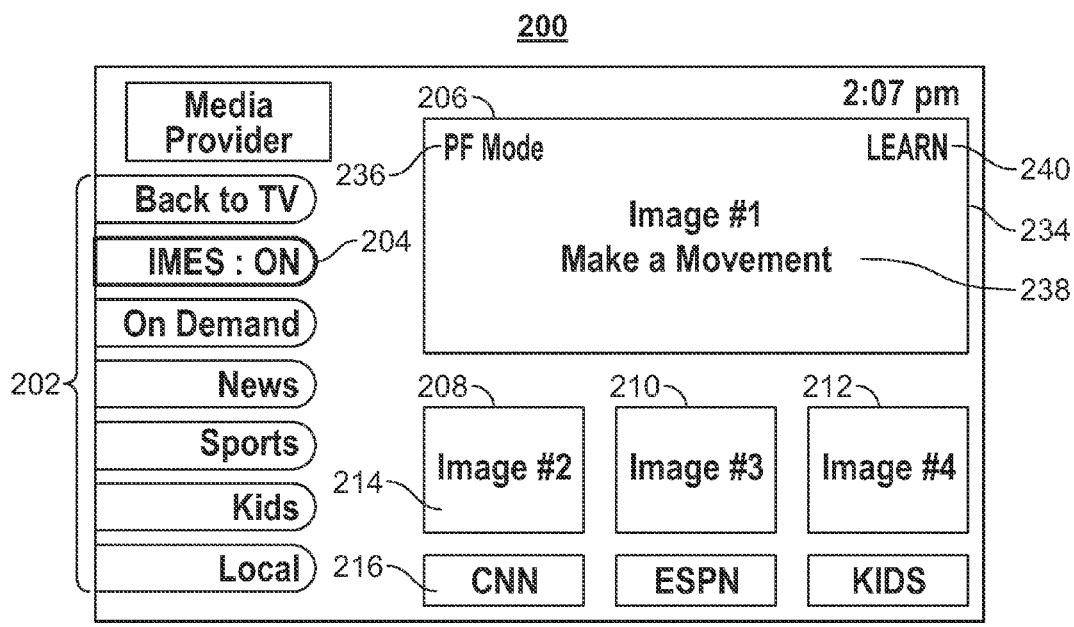
FIG. 2 shows an illustrative media guidance application that may be used to adjust user settings in accordance with some embodiments of the disclosure.

FIGS. 1-2 show illustrative display screens that may be used to provide media guidance data. The display screens shown in FIGS. 1-2 may be implemented on any suitable user equipment device or platform. While the displays of FIGS. 1-2 are illustrated as full screen displays, they may also be fully or partially overlaid over content being displayed. A user may indicate a desire to access content information by selecting a selectable option provided in a display screen (e.g., a menu option, a listings option, an icon, a hyperlink, etc.) or pressing a dedicated button (e.g., a GUIDE button) on a remote control or other user input interface or device. In response to the user's indication, the media guidance application may provide a display screen with media guidance data organized in one of several ways, such as by time and channel in a grid, by time, by channel, by source, by content type, by category (e.g., movies, sports, news, children, or other categories of programming), or other predefined, user-defined, or other organization criteria.

FIG. 1 shows illustrative grid program listings display 100 arranged by time and channel that also enables access to different types of content in a single display. Display 100 may include grid 102 with: (1) a column of channel/content type identifiers 104, where each channel/content type identifier (which is a cell in the column) identifies a different channel or content type available; and (2) a row of time identifiers 106, where each time identifier (which is a cell in the row) identifies a time block of programming. Grid 102 also includes cells of program listings, such as program listing 108, where each listing provides the title of the program provided on the listing's associated channel and time. With a user input device, a user can select program listings by moving highlight region 110. Information relating to the program listing selected by moving highlight region 110 may be provided in program information region 112. Program information region 112 may include, for example, the program title, the program description, the time the program is provided (if applicable), the channel the program is on (if applicable), the program's rating, and other desired information.

In addition to providing access to linear programming (e.g., content that is scheduled to be transmitted to a plurality of user equipment devices at a predetermined time and is provided according to a schedule), the media guidance application also provides access to non-linear programming (e.g., content accessible to a user equipment device at any time and is not provided according to a schedule). Non-linear programming may include content from different content sources including on-demand content (e.g., VOD), Internet content (e.g., streaming media, downloadable media, etc.), locally stored content (e.g., content stored on any user equipment device described above or other storage device), or other time-independent content. On-demand content may include movies or any other content provided by a particular content provider (e.g., HBO On Demand providing "The Sopranos" and "Curb Your Enthusiasm"). HBO ON DEMAND is a service mark owned by Time Warner Company L.P. et al. and THE SOPRANOS and CURB YOUR ENTHUSIASM are trademarks owned by the Home Box Office, Inc. Internet content may include web events, such as a chat session or Webcast, or content available on-demand as streaming content or downloadable content through an Internet web site or other Internet access (e.g. FTP).

Grid 102 may provide media guidance data for non-linear programming including on-demand listing 114, recorded content listing 116, and Internet content listing 118. A display combining media guidance data for content from different types of content sources is sometimes referred to as a "mixed-media" display. Various permutations of the types of media guidance data that may be displayed that are different than display 100 may be based on user selection or guidance application definition (e.g., a display of only recorded and broadcast listings, only on-demand and broadcast listings, etc.). As illustrated, listings 114, 116, and 118 are shown as spanning the entire time block displayed in grid 102 to indicate that selection of these listings may provide access to a display dedicated to on-demand listings, recorded listings, or Internet listings, respectively. In some embodiments, listings for these content types may be included directly in grid 102. Additional media guidance data may be displayed in response to the user selecting one of the navigational icons 120. (Pressing an arrow key on a user input device may affect the display in a similar manner as selecting navigational icons 120.)

Display 100 may also include video region 122, advertisement 124, and options region 126. Video region 122 may allow the user to view and/or preview programs that are currently available, will be available, or were available to the user. The content of video region 122 may correspond to, or be independent from, one of the listings displayed in grid 102. Grid displays including a video region are sometimes referred to as picture-in-guide (PIG) displays. PIG displays and their functionalities are described in greater detail in Satterfield et al. U.S. Pat. No. 6,564,378, issued May 13, 2003 and Yuen et al. U.S. Pat. No. 6,239,794, issued May 29, 2001, which are hereby incorporated by reference herein in their entireties. PIG displays may be included in other media guidance application display screens of the embodiments described herein.

Advertisement 124 may provide an advertisement for content that, depending on a viewer's access rights (e.g., for subscription programming), is currently available for viewing, will be available for viewing in the future, or may never become available for viewing, and may correspond to or be unrelated to one or more of the content listings in grid 102. Advertisement 124 may also be for products or services related or unrelated to the content displayed in grid 102. Advertisement 124 may be selectable and provide further information about content, provide information about a product or a service, enable purchasing of content, a product, or a service, provide content relating to the advertisement, etc. Advertisement 124 may be targeted based on a user's profile/preferences, monitored user activity, the type of display provided, or on other suitable targeted advertisement bases.

While advertisement 124 is shown as rectangular or banner shaped, advertisements may be provided in any suitable size, shape, and location in a guidance application display. For example, advertisement 124 may be provided as a rectangular shape that is horizontally adjacent to grid 102. This is sometimes referred to as a panel advertisement. In addition, advertisements may be overlaid over content or a guidance application display or embedded within a display. Advertisements may also include text, images, rotating images, video clips, or other types of content described above. Advertisements may be stored in a user equipment device having a guidance application, in a database connected to the user equipment, in a remote location (including streaming media servers), or on other storage means, or a combination of these locations. Providing advertisements in a media guidance application is discussed in greater detail in, for example, Knudson et al., U.S. Patent Application Publication No. 2003/0110499, filed Jan. 17, 2003; Ward, I I I et al. U.S. Pat. No. 6,756,997, issued Jun. 29, 2004; and Schein et al. U.S. Pat. No. 6,388,714, issued May 14, 2002, which are hereby incorporated by reference herein in their entireties. It will be appreciated that advertisements may be included in other media guidance application display screens of the embodiments described herein.

Options region 126 may allow the user to access different types of content, media guidance application displays, and/or media guidance application features. Options region 126 may be part of display 100 (and other display screens described herein), or may be invoked by a user by selecting an on-screen option or pressing a dedicated or assignable button on a user input device. The selectable options within options region 126 may concern features related to program listings in grid 102 or may include options available from a main menu display. Features related to program listings may include searching for other air times or ways of receiving a program, recording a program, enabling series recording of a program, setting program and/or channel as a favorite, purchasing a program, or other features. Options available from a main menu display may include search options, VOD options, parental control options, Internet options, cloud-based options, device synchronization options, second screen device options, options to access various types of media guidance data displays, options to subscribe to a premium service, options to edit a user's profile, options to access a browse overlay, or other options.

The media guidance application may be personalized based on a user's preferences. A personalized media guidance application allows a user to customize displays and features to create a personalized "experience" with the media guidance application. This personalized experience may be created by allowing a user to input these customizations and/or by the media guidance application monitoring user activity to determine various user preferences. Users may access their personalized guidance application by logging in or otherwise identifying themselves to the guidance application. Customization of the media guidance application may be made in accordance with a user profile. The customizations may include varying presentation schemes (e.g., color scheme of displays, font size of text, etc.), aspects of content listings displayed (e.g., only HDTV or only 3D programming, user-specified broadcast channels based on favorite channel selections, re-ordering the display of channels, recommended content, etc.), desired recording features (e.g., recording or series recordings for particular users, recording quality, etc.), parental control settings, customized presentation of Internet content (e.g., presentation of social media content, e-mail, electronically delivered articles, etc.) and other desired customizations.

The media guidance application may allow a user to provide user profile information or may automatically compile user profile information. The media guidance application may, for example, monitor the content the user accesses and/or other interactions the user may have with the guidance application. Additionally, the media guidance application may obtain all or part of other user profiles that are related to a particular user (e.g., from other web sites on the Internet the user accesses, such as www.allrovi.com, from other media guidance applications the user accesses, from other interactive applications the user accesses, from another user equipment device of the user, etc.), and/or obtain information about the user from other sources that the media guidance application may access. As a result, a user can be provided with a unified guidance application experience across the user's different user equipment devices. This type of user experience is described in greater detail below in connection with FIG. 4. Additional personalized media guidance application features are described in greater detail in Ellis et al., U.S. Patent Application Publication No. 2005/0251827, filed Jul. 11, 2005, Boyer et al., U.S. Pat. No. 7,165,098, issued Jan. 16, 2007, and Ellis et al., U.S. Patent Application Publication No. 2002/0174430, filed Feb. 21, 2002, which are hereby incorporated by reference herein in their entireties.

FIG. 1 shows an illustrative media guidance application for selecting media assets featuring an on-screen icon associated with an attempted motion of the user. For example, in some embodiments, the media guidance application may generate a display of an on-screen icon that provides instructions to the user, allowing the user to learn how to control the media guidance application through his or her attempted motions. For example, in order to a provide a user with guidance related to performing media guidance application operations using their electrical impulses to missing appendages ("phantom" limbs) as recorded in an EEG pattern, the media guidance application may provide instructions as to what movements the user may attempt. As shown in FIG. 1, in window 134, indicators 136 and 140 are displayed to the user, indicating that the prosthetic free "PF" mode is "ON." As noted above, a user may interact with the media guidance application when the "PF" mode is "ON", either with the prosthetic worn and connected or with the prosthetic disconnected from the user's body, as long as a user device is connected and recognized by the media guidance application (see FIG. 2). In addition, a schematic indicator 132, e.g. a left-to-right arrow is displayed, along with instructions 138, e.g. "swipe your index finger to scroll," suggesting to the user through both text and image, a command to be executed. In this example, a user may learn how to scroll through media listings by intending to move their phantom index finger from left to right. In some example, a user profile may include information inputted by the user regarding their IMES (implantable myoelectric sensor) device type and characteristics, along with which type of prosthetic the user has, e.g. a finger, hand, arm, leg, etc. For example, the gestures suggested by the PF learn mode may be customized to a type of phantom limb, or a type of sensing device in use by the user. In some embodiments the PF learn mode may be automatically active, for example for the first few days or weeks following the first PF mode activation. In some embodiments, users may request PF learn mode at any time during their interaction with the media guidance application. Furthermore, users may access and view a database of intended motions and corresponding media guidance application operations, for example as shown in window 134. For example, the database may be updated periodically, or at the user's request. Furthermore, the database may be customized to a specific user.

Another display arrangement for providing media guidance is shown in FIG. 2. Video mosaic display 200 includes selectable options 202 for content information organized based on content type, genre, and/or other organization criteria. In video mosaic display 200, selectable option 204 is selected, indicating that the IMES device is on and recognized by the media guidance application system, such that the media guidance application system and the IMES device may communicate, regardless of the presence of the prosthetic on the user's remaining limb. As shown in video mosaic display 200 and represented by icon 236, the prosthetic free ("PF") mode is on, thereby initiating, when an IMES device is detected and recognized, monitoring signals from the IMES device, such that a user's brain activity and/or myoelectric signals at the user's remaining limb may be processed, and associated with an EEG signature or pattern. In some embodiments, selecting selectable option 204 may switch a user device configured to monitor the brain activity of a user from a first mode (e.g. a "sleep mode") to a second mode (e.g., an "active mode"). This is further described in U.S. patent application Ser. No. 14/038,158, hereby incorporated by reference herein in its entirety. In response to selectable option 204 being selected, the media guidance application may also generate a display of icon 240, which may indicate that a learning mode is activated, with instructions 238 displayed within window 234. For example, the media guidance application may prompt a user with the prosthetic free mode on, and in learning mode, to attempt a movement of their phantom limb, such that the attempted movement may be associated with a media guidance application operation and stored in a database.

In video mosaic display 200 listings may provide graphical images including cover art, still images from the content, video clip previews, live video from the content, or other types of content that indicate to a user the content being described by the media guidance data in the listing. Each of the graphical listings may also be accompanied by text to provide further information about the content associated with the listing. For example, listing 208 may include more than one portion, including media portion 214 and text portion 216. Media portion 214 and/or text portion 216 may be selectable to view content in full-screen or to view information related to the content displayed in media portion 214 (e.g., to view listings for the channel that the video is displayed on).

The listings in video mosaic display 200 are of different sizes (i.e., listing 206 is larger than listings 208, 210, and 212), but if desired, all the listings may be the same size. Listings may be of different sizes or graphically accentuated to indicate degrees of interest to the user or to emphasize certain content, as desired by the content provider or based on user preferences. Various systems and methods for graphically accentuating content listings are discussed in, for example, Yates, U.S. Patent Application Publication No. 2010/0153885, filed Dec. 29, 2005, which is hereby incorporated by reference herein in its entirety.

Figure 3:
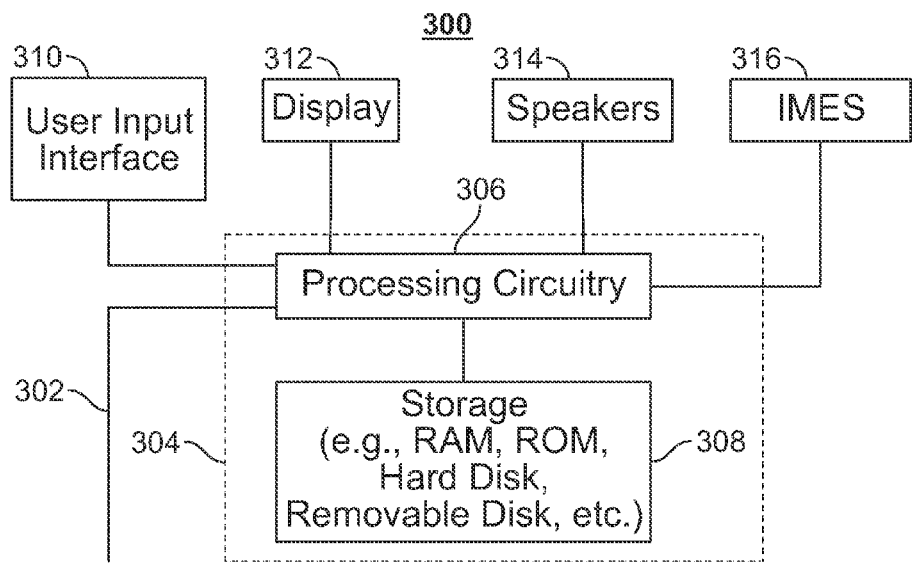
FIG. 3 is a block diagram of an illustrative media system in accordance with some embodiments of the disclosure.

Users may access content and the media guidance application (and its display screens described above and below) from one or more of their user equipment devices. FIG. 3 shows a generalized embodiment of illustrative user equipment device 300. More specific implementations of user equipment devices are discussed below in connection with FIG. 4. Illustrative user equipment device 300 may receive content and data via input/output (hereinafter "I/O") I/O path 302. I/O path 302 may provide content (e.g., broadcast programming, on-demand programming, Internet content, content available over a local area network (LAN) or wide area network (WAN), and/or other content) and data to control circuitry 304, which includes processing circuitry 306 and storage 308. Control circuitry 304 may be used to send and receive commands, requests, and other suitable data using I/O path 302. I/O path 302 may connect control circuitry 304 (and processing circuitry 306) to one or more communications paths (described below). I/O functions may be provided by one or more of these communications paths, but are shown as a single path in FIG. 3 to avoid overcomplicating the drawing.

Control circuitry 304 may be based on any suitable processing circuitry such as processing circuitry 306. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 304 executes instructions for a media guidance application stored in memory (i.e., storage 308). Specifically, control circuitry 304 may be instructed by the media guidance application to perform the functions discussed above and below. For example, the media guidance application may provide instructions to control circuitry 304 to generate the media guidance displays. In some implementations, any action performed by control circuitry 304 may be based on instructions received from the media guidance application.

In client-server based embodiments, control circuitry 304 may include communications circuitry suitable for communicating with a guidance application server or other networks or servers. The instructions for carrying out the above mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths (which is described in more detail in connection with FIG. 4). In addition, communications circuitry may include circuitry that enables peer-to-peer communication of user equipment devices, or communication of user equipment devices in locations remote from each other (described in more detail below).

Memory may be an electronic storage device provided as storage 308 that is part of control circuitry 304. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 308 may be used to store various types of content described herein as well as media guidance data described above. Nonvolatile memory may also be used (e.g., to launch a boot-up routine and other instructions). Cloud-based storage, described in relation to FIG. 4, may be used to supplement storage 308 or instead of storage 308.

Control circuitry 304 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 304 may also include scaler circuitry for upconverting and downconverting content into the preferred output format of the illustrative user equipment device 300. Control circuitry 304 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions (e.g., watch and record functions, picture-in-picture (PIP) functions, multiple-tuner recording, etc.). If storage 308 is provided as a separate device from illustrative user equipment device 300, the tuning and encoding circuitry (including multiple tuners) may be associated with storage 308.

A user may send instructions to control circuitry 304 using user input interface 310. User input interface 310 may be any suitable user interface, such as a remote control, mouse, trackball, keypad, keyboard, touch screen, touchpad, stylus input, joystick, voice recognition interface, or other user input interfaces. Display 312 may be provided as a stand-alone device or integrated with other elements of illustrative user equipment device 300. For example, display 312 may be a touchscreen or touch-sensitive display. In such circumstances, user input interface 310 may be integrated with or combined with display 312. Display 312 may be one or more of a monitor, a television, a liquid crystal display (LCD) for a mobile device, amorphous silicon display, low temperature poly silicon display, electronic ink display, electrophoretic display, active matrix display, electro-wetting display, electrofluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, display 312 may be HDTV-capable. In some embodiments, display 312 may be a 3D display, and the interactive media guidance application and any suitable content may be displayed in 3D. A video card or graphics card may generate the output to the display 312. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 304. The video card may be integrated with the control circuitry 304. Speakers 314 may be provided as integrated with other elements of illustrative user equipment device 300 or may be stand-alone units. The audio component of videos and other content displayed on display 312 may be played through speakers 314. In some embodiments, the audio may be distributed to a receiver (not shown), which processes and outputs the audio via speakers 314.

Control circuitry 304 may also instruct IMES component 316. IMES component 316 of a user device may include one or more additional sub-components (e.g., an EEG, EMG, multiple sensors, telemetry controller etc.) for monitoring brain activity of a user and a user's intended motion. IMES component 316 may transmit updates (e.g., associated with brain activity and intended motions) of a user to control circuitry 304. Control circuitry 304 may compare the updates to data related to brain activity (e.g., threshold ranges, frequency ranges, associated with EMG signatures etc.) of the user and/or other users stored on storage 308 (e.g., to determine whether or not the EMG signature or brain activity of the user corresponds to a particular EMG signature or pattern, etc.).

It should be noted, IMES component 316 and/or any of its sub-components (e.g., an EEG, EMG, multiple sensors, telemetry controller, etc.) may, in some embodiments, be located on a separate device in communication with the device upon which a media guidance application (and control circuitry 304) is implemented. For example, in some embodiments, monitoring IMES components 316 may communication with illustrative user equipment device 300 via a communications network (e.g., communications network 414 (FIG. 4)).

The guidance application may be implemented using any suitable architecture. For example, it may be a stand-alone application wholly implemented on illustrative user equipment device 300. In such an approach, instructions of the application are stored locally (e.g., in storage 308), and data for use by the application is downloaded on a periodic basis (e.g., from an out-of-band feed, from an Internet resource, or using another suitable approach). Control circuitry 304 may retrieve instructions of the application from storage 308 and process the instructions to generate any of the displays discussed herein. Based on the processed instructions, control circuitry 304 may determine what action to perform when input is received from user input interface 310. For example, movement of a cursor on a display up/down may be indicated by the processed instructions when user input interface 310 indicates that an up/down button was selected.

In some embodiments, the media guidance application is a client-server based application. Data for use by a thick or thin client implemented on illustrative user equipment device 300 is retrieved on-demand by issuing requests to a server remote to the illustrative user equipment device 300. In one example of a client-server based guidance application, control circuitry 304 runs a web browser that interprets web pages provided by a remote server. For example, the remote server may store the instructions for the application in a storage device. The remote server may process the stored instructions using circuitry (e.g., control circuitry 304) and generate the displays discussed above and below. The client device may receive the displays generated by the remote server and may display the content of the displays locally on illustrative user equipment device 300. This way, the processing of the instructions is performed remotely by the server while the resulting displays are provided locally on illustrative user equipment device 300. Illustrative user equipment device 300 may receive inputs from the user via user input interface 310 and transmit those inputs to the remote server for processing and generating the corresponding displays. For example, illustrative user equipment device 300 may transmit a communication to the remote server indicating that an up/down button was selected via user input interface 310. The remote server may process instructions in accordance with that input and generate a display of the application corresponding to the input (e.g., a display that moves a cursor up/down). The generated display is then transmitted to illustrative user equipment device 300 for presentation to the user.

In some embodiments, the media guidance application is downloaded and interpreted or otherwise run by an interpreter or virtual machine (run by control circuitry 304). In some embodiments, the guidance application may be encoded in the ETV Binary Interchange Format (EBIF), received by control circuitry 304 as part of a suitable feed, and interpreted by a user agent running on control circuitry 304. For example, the guidance application may be an EBIF application. In some embodiments, the guidance application may be defined by a series of JAVA-based files that are received and run by a local virtual machine or other suitable middleware executed by control circuitry 304. In some of such embodiments (e.g., those employing MPEG-2 or other digital media encoding schemes), the guidance application may be, for example, encoded and transmitted in an MPEG-2 object carousel with the MPEG audio and video packets of a program.

Figure 4:
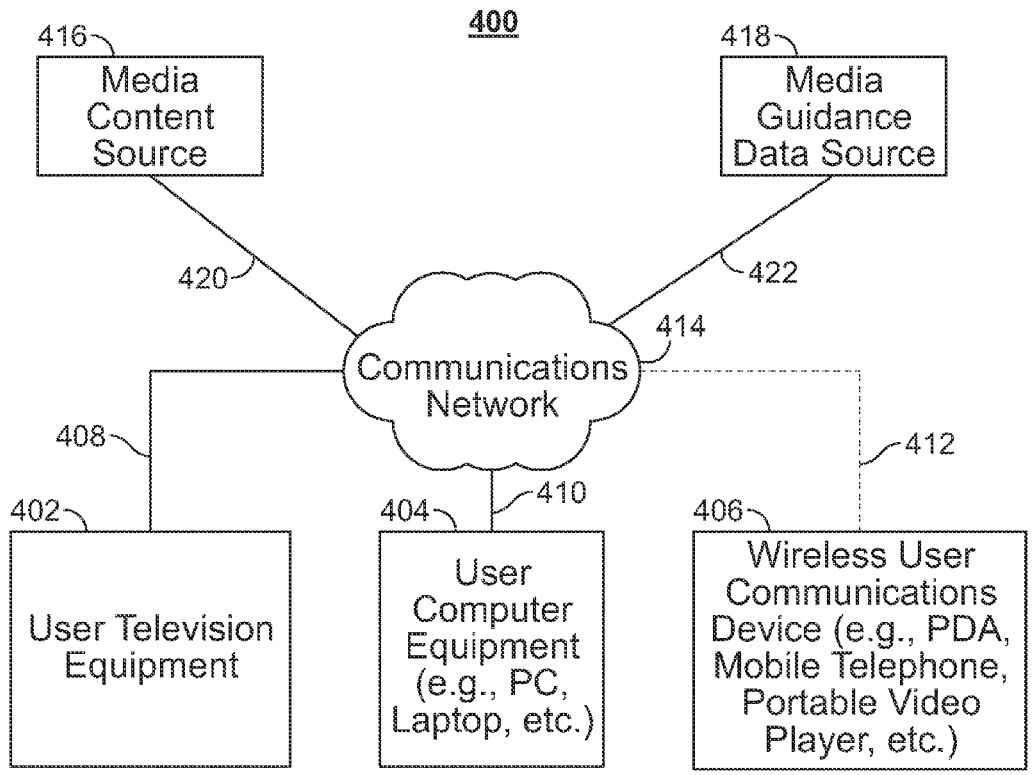
FIG. 4 is a block diagram of an illustrative media system in accordance with some embodiments of the disclosure.

Illustrative user equipment device 300 of FIG. 3 can be implemented in media guidance system 400 of FIG. 4 as user television equipment 402, user computer equipment 404, wireless user communications device 406, or any other type of user equipment suitable for accessing content, such as a non-portable gaming machine. For simplicity, these devices may be referred to herein collectively as user equipment or user equipment devices, and may be substantially similar to user equipment devices described above. User equipment devices, on which a media guidance application may be implemented, may function as a standalone device or may be part of a network of devices. Various network configurations of devices may be implemented and are discussed in more detail below.

A user equipment device utilizing at least some of the system features described above in connection with FIG. 3 may not be classified solely as user television equipment 402, user computer equipment 404, or a wireless user communications device 406. For example, user television equipment 402 may, like some user computer equipment 404, be Internet-enabled allowing for access to Internet content, while user computer equipment 404 may, like some user television equipment 402, include a tuner allowing for access to television programming. The media guidance application may have the same layout on various different types of user equipment or may be tailored to the display capabilities of the user equipment. For example, on user computer equipment 404, the guidance application may be provided as a web site accessed by a web browser. In another example, the guidance application may be scaled down for wireless user communications devices 406.

In media guidance system 400, there is typically more than one of each type of user equipment device but only one of each is shown in FIG. 4 to avoid overcomplicating the drawing. In addition, each user may utilize more than one type of user equipment device and also more than one of each type of user equipment device.

In some embodiments, a user equipment device (e.g., user television equipment 402, user computer equipment 404, wireless user communications device 406) may be referred to as a "second screen device." For example, a second screen device may supplement content presented on a first user equipment device. The content presented on the second screen device may be any suitable content that supplements the content presented on the first device. In some embodiments, the second screen device provides an interface for adjusting settings and display preferences of the first device. In some embodiments, the second screen device is configured for interacting with other second screen devices or for interacting with a social network. The second screen device can be located in the same room as the first device, a different room from the first device but in the same house or building, or in a different building from the first device.

The user may also set various settings to maintain consistent media guidance application settings across in-home devices and remote devices. Settings include those described herein, as well as channel and program favorites, programming preferences that the guidance application utilizes to make programming recommendations, display preferences, and other desirable guidance settings. For example, if a user sets a channel as a favorite on, for example, the web site www.allrovi.com on their personal computer at their office, the same channel would appear as a favorite on the user's in-home devices (e.g., user television equipment and user computer equipment) as well as the user's mobile devices, if desired. Therefore, changes made on one user equipment device can change the guidance experience on another user equipment device, regardless of whether they are the same or a different type of user equipment device. In addition, the changes made may be based on settings input by a user, as well as user activity monitored by the guidance application.

The user equipment devices may be coupled to communications network 414. Namely, user television equipment 402, user computer equipment 404, and wireless user communications device 406 are coupled to communications network 414 via communications paths 408, 410, and 412, respectively. Communications network 414 may be one or more networks including the Internet, a mobile phone network, mobile voice or data network (e.g., a 4G or LTE network), cable network, public switched telephone network, or other types of communications network or combinations of communications networks. Paths 408, 410, and 412 may separately or together include one or more communications paths, such as, a satellite path, a fiber-optic path, a cable path, a path that supports Internet communications (e.g., IPTV), free-space connections (e.g., for broadcast or other wireless signals), or any other suitable wired or wireless communications path or combination of such paths. Path 412 is drawn with dotted lines to indicate that in the exemplary embodiment shown in FIG. 4 it is a wireless path and paths 408 and 410 are drawn as solid lines to indicate they are wired paths (although these paths may be wireless paths, if desired). Communications with the user equipment devices may be provided by one or more of these communications paths, but are shown as a single path in FIG. 4 to avoid overcomplicating the drawing.

Although communications paths are not drawn between user equipment devices, these devices may communicate directly with each other via communication paths, such as those described above in connection with paths 408, 410, and 412, as well as other short-range point-to-point communication paths, such as USB cables, IEEE 1394 cables, wireless paths (e.g., Bluetooth, infrared, IEEE 802-11x, etc.), or other short-range communication via wired or wireless paths. BLUETOOTH is a certification mark owned by Bluetooth SIG, INC. The user equipment devices may also communicate with each other directly through an indirect path via communications network 414.

Media guidance system 400 includes content source 416 and media guidance data source 418 coupled to communications network 414 via communication paths 420 and 422, respectively. Paths 420 and 422 may include any of the communication paths described above in connection with paths 408, 410, and 412. Communications with the content source 416 and media guidance data source 418 may be exchanged over one or more communications paths, but are shown as a single path in FIG. 4 to avoid overcomplicating the drawing. In addition, there may be more than one of each of content source 416 and media guidance data source 418, but only one of each is shown in FIG. 4 to avoid overcomplicating the drawing. (The different types of each of these sources are discussed below.) If desired, content source 416 and media guidance data source 418 may be integrated as one source device. Although communications between content source 416 and media guidance data source 418 with user equipment devices 402, 404, and 406 are shown as through communications network 414, in some embodiments, content source 416 and media guidance data source 418 may communicate directly with user television equipment devices 402, 404, and 406 via communication paths (not shown) such as those described above in connection with paths 408, 410, and 412.

Content source 416 may include one or more types of content distribution equipment including a television distribution facility, cable system headend, satellite distribution facility, programming sources (e.g., television broadcasters, such as NBC, ABC, HBO, etc.), intermediate distribution facilities and/or servers, Internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Content source 416 may be the originator of content (e.g., a television broadcaster, a Webcast provider, etc.) or may not be the originator of content (e.g., an on-demand content provider, an Internet provider of content of broadcast programs for downloading, etc.). Content source 416 may include cable sources, satellite providers, on-demand providers, Internet providers, over-the-top content providers, or other providers of content. Content source 416 may also include a remote media server used to store different types of content (including video content selected by a user), in a location remote from any of the user equipment devices. Systems and methods for remote storage of content, and providing remotely stored content to user equipment are discussed in greater detail in connection with Ellis et al., U.S. Pat. No. 7,761,892, issued Jul. 20, 2010, which is hereby incorporated by reference herein in its entirety.

Media guidance data source 418 may provide media guidance data, such as the media guidance data described above. Media guidance data may be provided to the user equipment devices using any suitable approach. In some embodiments, the guidance application may be a stand-alone interactive television program guide that receives program guide data via a data feed (e.g., a continuous feed or trickle feed). Program schedule data and other guidance data may be provided to the user equipment on a television channel sideband, using an in-band digital signal, using an out-of-band digital signal, or by any other suitable data transmission technique. Program schedule data and other media guidance data may be provided to user equipment on multiple analog or digital television channels.

In some embodiments, guidance data from media guidance data source 418 may be provided to users' equipment using a client-server approach. For example, a user equipment device may pull media guidance data from a server, or a server may push media guidance data to a user equipment device. In some embodiments, a guidance application client residing on the user's equipment may initiate sessions with source 418 to obtain guidance data when needed, e.g., when the guidance data is out of date or when the user equipment device receives a request from the user to receive data. Media guidance may be provided to the user equipment with any suitable frequency (e.g., continuously, daily, a user-specified period of time, a system-specified period of time, in response to a request from user equipment, etc.). Media guidance data source 418 may provide user equipment devices 402, 404, and 406 the media guidance application itself or software updates for the media guidance application.

In some embodiments, the media guidance data may include viewer data. For example, the viewer data may include current and/or historical user activity information (e.g., what content the user typically watches, what times of day the user watches content, whether the user interacts with a social network, at what times the user interacts with a social network to post information, what types of content the user typically watches (e.g., pay TV or free TV), mood, brain activity information, etc.). The media guidance data may also include subscription data. For example, the subscription data may identify to which sources or services a given user subscribes and/or to which sources or services the given user has previously subscribed but later terminated access (e.g., whether the user subscribes to premium channels, whether the user has added a premium level of services, whether the user has increased Internet speed). In some embodiments, the viewer data and/or the subscription data may identify patterns of a given user for a period of more than one year. The media guidance data may include a model (e.g., a survivor model) used for generating a score that indicates a likelihood a given user will terminate access to a service/source. For example, the media guidance application may process the viewer data with the subscription data using the model to generate a value or score that indicates a likelihood of whether the given user will terminate access to a particular service or source. In particular, a higher score may indicate a higher level of confidence that the user will terminate access to a particular service or source. Based on the score, the media guidance application may generate promotions and advertisements that entice the user to keep the particular service or source indicated by the score as one to which the user will likely terminate access.

Media guidance applications may be, for example, stand-alone applications implemented on user equipment devices. For example, the media guidance application may be implemented as software or a set of executable instructions which may be stored in storage 308, and executed by control circuitry 304 of illustrative user equipment device 300. In some embodiments, media guidance applications may be client-server applications where only a client application resides on the user equipment device, and server application resides on a remote server. For example, media guidance applications may be implemented partially as a client application on control circuitry 304 of illustrative user equipment device 300 and partially on a remote server as a server application (e.g., media guidance data source 418) running on control circuitry of the remote server. When executed by control circuitry of the remote server (such as media guidance data source 418), the media guidance application may instruct the control circuitry to generate the guidance application displays and transmit the generated displays to the user equipment devices. The server application may instruct the control circuitry of the media guidance data source 418 to transmit data for storage on the user equipment. The client application may instruct control circuitry of the receiving user equipment to generate the guidance application displays.

Content and/or media guidance data delivered to user television equipment devices 402, 404, and 406 may be over-the-top (OTT) content. OTT content delivery allows Internet-enabled user devices, including any user equipment device described above, to receive content that is transferred over the Internet, including any content described above, in addition to content received over cable or satellite connections. OTT content is delivered via an Internet connection provided by an Internet service provider (ISP), but a third party distributes the content. The ISP may not be responsible for the viewing abilities, copyrights, or redistribution of the content, and may only transfer IP packets provided by the OTT content provider. Examples of OTT content providers include YOUTUBE, NETFLIX, and HULU, which provide audio and video via IP packets. Youtube is a trademark owned by Google Inc., Netflix is a trademark owned by Netflix Inc., and Hulu is a trademark owned by Hulu, LLC. OTT content providers may additionally or alternatively provide media guidance data described above. In addition to content and/or media guidance data, providers of OTT content can distribute media guidance applications (e.g., web-based applications or cloud-based applications), or the content can be displayed by media guidance applications stored on the user equipment device.

Media guidance system 400 is intended to illustrate a number of approaches, or network configurations, by which user equipment devices and sources of content and guidance data may communicate with each other for the purpose of accessing content and providing media guidance. The embodiments described herein may be applied in any one or a subset of these approaches, or in a system employing other approaches for delivering content and providing media guidance. The following four approaches provide specific illustrations of the generalized example of FIG. 4.

In one approach, user equipment devices may communicate with each other within a home network. User equipment devices can communicate with each other directly via short-range point-to-point communication schemes described above, via indirect paths through a hub or other similar device provided on a home network, or via communications network 414. Each of the multiple individuals in a single home may operate different user equipment devices on the home network. As a result, it may be desirable for various media guidance information or settings to be communicated between the different user equipment devices. For example, it may be desirable for users to maintain consistent media guidance application settings on different user equipment devices within a home network, as described in greater detail in Ellis et al., U.S. patent application Ser. No. 11/179,410, filed Jul. 11, 2005. Different types of user equipment devices in a home network may also communicate with each other to transmit content. For example, a user may transmit content from user computer equipment to a portable video player or portable music player.

In a second approach, users may have multiple types of user equipment by which they access content and obtain media guidance. For example, some users may have home networks that are accessed by in-home and mobile devices. Users may control in-home devices via a media guidance application implemented on a remote device. For example, users may access an online media guidance application on a website via a personal computer at their office, or a mobile device such as a PDA or web-enabled mobile telephone. The user may set various settings (e.g., recordings, reminders, or other settings) on the online guidance application to control the user's in-home equipment. The online guide may control the user's equipment directly, or by communicating with a media guidance application on the user's in-home equipment. Various systems and methods for user equipment devices communicating, where the user equipment devices are in locations remote from each other, is discussed in, for example, Ellis et al., U.S. Pat. No. 8,046,801, issued Oct. 25, 2011, which is hereby incorporated by reference herein in its entirety.

In a third approach, users of user equipment devices inside and outside a home can use their media guidance application to communicate directly with content source 416 to access content. Specifically, within a home, users of user television equipment 402 and user computer equipment 404 may access the media guidance application to navigate among and locate desirable content. Users may also access the media guidance application outside of the home using wireless user communications devices 406 to navigate among and locate desirable content.

In a fourth approach, user equipment devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices, which may be located centrally or at distributed locations, that provide cloud-based services to various types of users and devices connected via a network such as the Internet via communications network 414. These cloud resources may include one or more content sources 416 and one or more media guidance data sources 418. In addition or in the alternative, the remote computing sites may include other user equipment devices, such as user television equipment 402, user computer equipment 404, and wireless user communications device 406. For example, the other user equipment devices may provide access to a stored copy of a video or a streamed video. In such embodiments, user equipment devices may operate in a peer-to-peer manner without communicating with a central server.

The cloud provides access to services, such as content storage, content sharing, or social networking services, among other examples, as well as access to any content described above, for user equipment devices. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user equipment device to store content to the cloud and to receive content from the cloud rather than storing content locally and accessing locally-stored content.

A user may use various content capture devices, such as camcorders, digital cameras with video mode, audio recorders, mobile phones, and handheld computing devices, to record content. The user can upload content to a content storage service on the cloud either directly, for example, from user computer equipment 404 or wireless user communications device 406 having content capture feature. Alternatively, the user can first transfer the content to a user equipment device, such as user computer equipment 404. The user equipment device storing the content uploads the content to the cloud using a data transmission service on communications network 414. In some embodiments, the user equipment device itself is a cloud resource, and other user equipment devices can access the content directly from the user equipment device on which the user stored the content.

Cloud resources may be accessed by a user equipment device using, for example, a web browser, a media guidance application, a desktop application, a mobile application, and/or any combination of access applications of the same. The user equipment device may be a cloud client that relies on cloud computing for application delivery, or the user equipment device may have some functionality without access to cloud resources. For example, some applications running on the user equipment device may be cloud applications, i.e., applications delivered as a service over the Internet, while other applications may be stored and run on the user equipment device. In some embodiments, a user device may receive content from multiple cloud resources simultaneously. For example, a user device can stream audio from one cloud resource while downloading content from a second cloud resource. Or a user device can download content from multiple cloud resources for more efficient downloading. In some embodiments, user equipment devices can use cloud resources for processing operations such as the processing operations performed by processing circuitry described in relation to FIG. 3.

Figure 5:
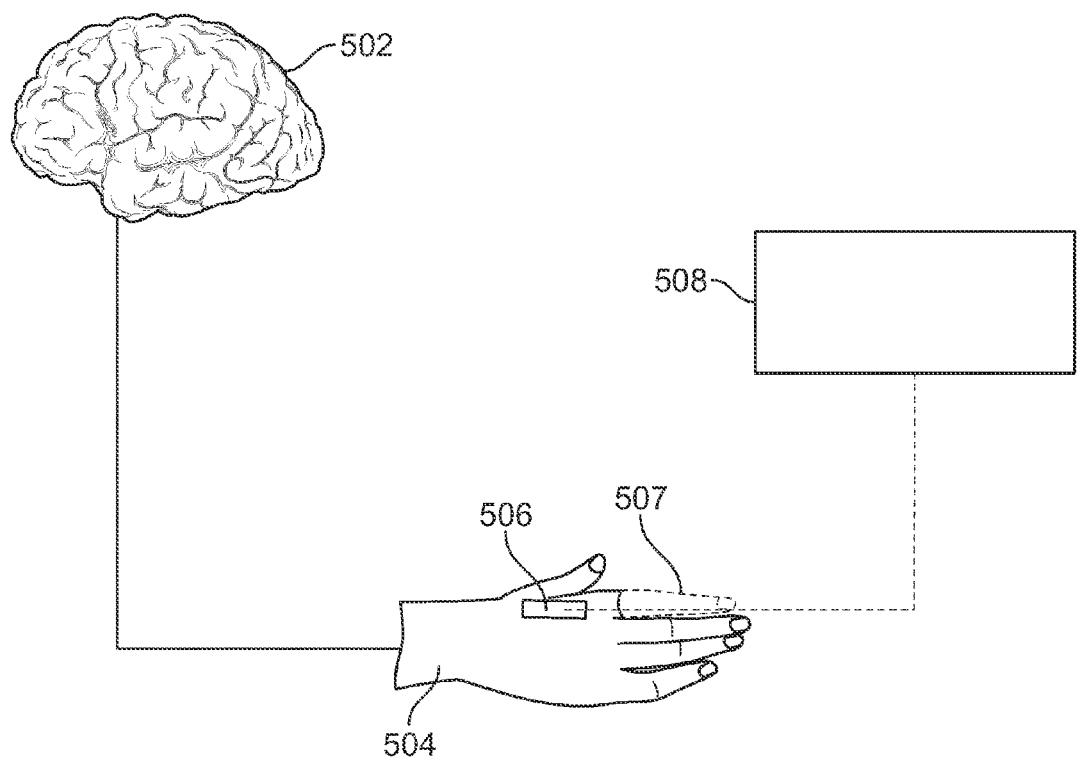
FIG. 5 shows a representation of a user and a user's missing limb which may be connected to a user device in accordance with some embodiments of the disclosure.

FIG. 5 shows an illustrative representation of a user and a user's missing limb which may be connected to a user device in accordance with some embodiments of the disclosure. For example, in some embodiments, a user may control a prosthetic through his or her brain activity. In the example shown in FIG. 5, the user's brain 502 is connected to the user remaining limb, e.g. arm and hand 504, with the user missing a portion or the entirety of the limb, e.g. missing limb or finger 507. For example, in FIG. 5, finger 507 is a "phantom" finger. For a wide ranger of practical or aesthetic reasons, users may have a prosthetic limb, e.g. an index finger prosthetic, but may desire based on personal preference and/or comfort to not wear the prosthetic at all times. For example, users may not desire to wear their prosthetic when relaxing on the couch or in bed. In FIG. 5, the user is not wearing any index finger prosthetic. Instead, the user may be resting his sore hand after a day of wearing the finger prosthetic at the office.

In FIG. 5 a device 506, such as implanted myoelectric sensors ("IMES") device 506 may connect to the user's prosthetic when the prosthetic is worn, but may also communicate with the media guidance application (or user device upon which the media guidance application is implemented) 508 even when the prosthetic is not worn, as shown in FIG. 5. In the event that the prosthetic is worn, signals received from the IMES device may be used to either control the prosthetic, and/or control the media guidance application through RF signals. In some examples, the user may select the dominant mode, such that prosthetic input (e.g. actions carried out by the prosthetic itself) or IMES device input (e.g. actions carried out as a result of processing the RF signal) may be the dominant input in the event of a conflict. Alternatively, the media guide application may include a default option with the prosthetic or IMES input as the dominant input in the event of conflicting instructions. In another example, control of the media guidance application system through the IMES device signals or the prosthetic actions may be mutually exclusive. For example, when the prosthetic is worn, the IMES device's capability to emit RF signals may be automatically disabled to avoid conflicts. In the example shown in FIG. 5 the user's brain may communicate with the arm 504 and sensors 506 by sending electrical signals to the muscles located at the base of the missing limb, e.g. index finger 507, replicating the electrical signals sent by a user to move the missing limb, e.g. an intended motion. The electrical signals recorded, measured, and/or processed by sensors 506 may form a distinct EMG signature, e.g. a pattern of signals, corresponding to the intended motion of the missing limb 507. In turn, the IMES device 506 may communicate the intended motion of the missing limb (e.g. finger) 507 to the media guidance application user device 508 through an RF signal.

In some embodiments, a telemetry controller may interface with the sensors to perform the processing of the myoelectric signals received. In some embodiments, the telemetry controller may be an intermediate device between sensors 506 and the missing limb, e.g. missing finger 507. For example, the telemetry controller may be integrated with sensing device 506, or may be a distinct device, located within a certain radius of the user. It should be noted that device 506 may include any additional sub-components for monitoring, processing and transmitting brain activity and associated intended motions, such as the afore-mentioned telemetry controller, electrodes, processing units, radio emitters, and storage devices. Similarly, media guidance application user device 508 may include any additional sub-components for receiving and processing RF signals.

In some embodiments, sensing devices 506 may be continuously monitoring the user's brain 502 and continuously receiving information forming an EEG signature. Alternatively, the user may turn on and off the ability of the sensors to detect myo-electrical signals, and/or turn on and off the ability of the sensors or associated component to send an RF signal encoding the received EEG signature.

Figure 6:
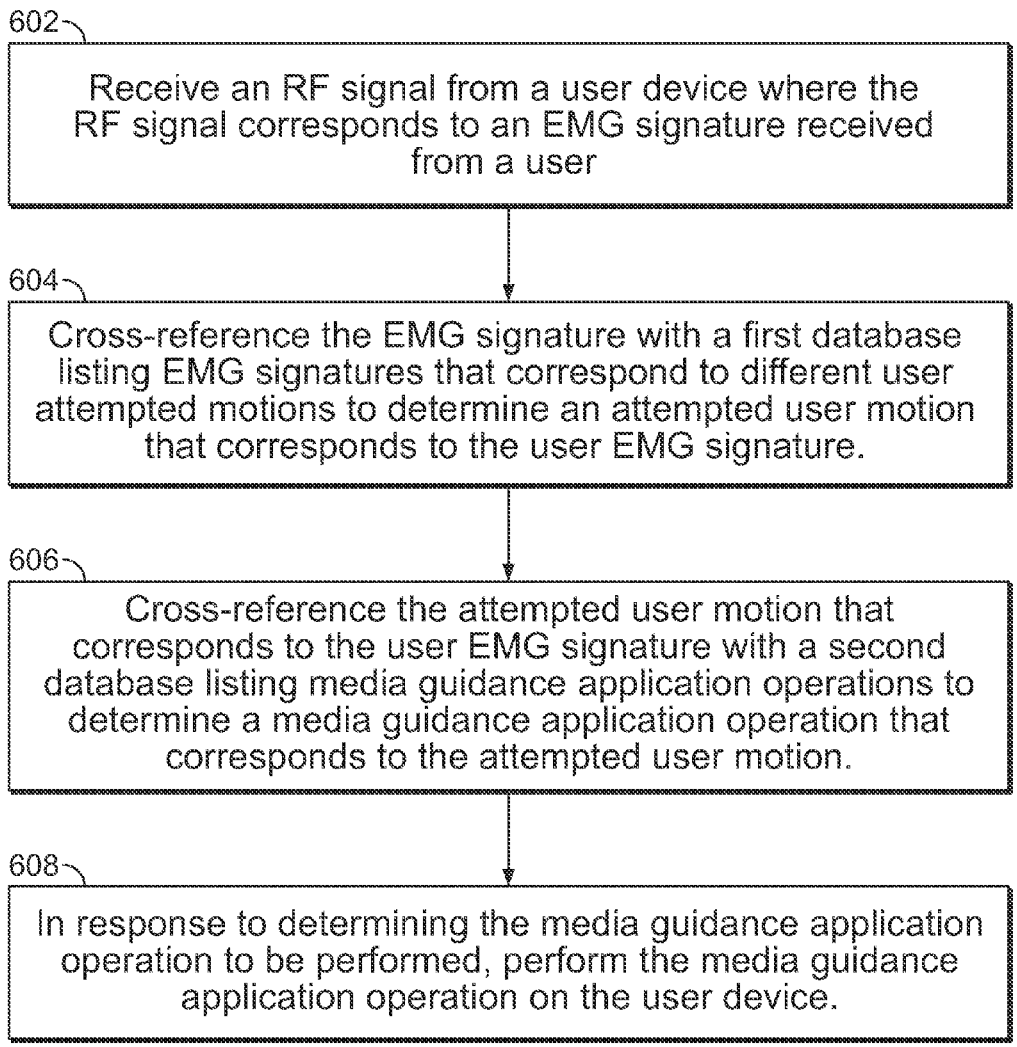
FIG. 6 is a flow-chart of illustrative steps involved in generating a media guidance application operation on a user device, in accordance with some embodiments of the disclosure.

FIG. 6 is a flow-chart of illustrative steps involved in generating a media guidance application operation on a user device, in accordance with some embodiments of the disclosure.

At step 602, the media guidance application (e.g. implemented on illustrative user equipment device 300 (FIG. 3)) receives an RF signal from a user device (e.g. IMES component 316 (FIG. 3) or sensor and/or telemetry components 506 (FIG. 5) where the RF signal corresponds to an EMG signature received from a user. For example, a user with an amputated arm is equipped with an IMES device (e.g. IMES component 316 (FIG. 3)) and an arm prosthetic, which can be controlled by the IMES device when the arm prosthetic is worn. The user's IMES device may include sensors (e.g. sensors 506 (FIG. 5)) which may receive an input from the user's brain in the form of myoelectric signals, and/or brain waves. The user's IMES device may process the user input into an EEG signature and/or unique pattern which may be converted into instructions to the prosthetic arm through electrical signals, radio signals, or any other connection. The user's IMES device may also convert the EEG signature and/or unique pattern and encode this information into RF signals or any other signals (e.g. wireless or cellular signals) which are emitted and which may be received by the media guidance application (e.g. implemented on illustrative user equipment device 300 (FIG. 3)).

At step 604, the media guidance application (e.g. processing circuitry 306 (FIG. 3)) cross-references the EMG signature with a first database (e.g. located in storage 308 (FIG. 3) and updated through a communications network 414 (FIG. 4)) listing EMG signatures that correspond to different user attempted motions to determine an attempted user motion that corresponds to the user EMG signature. For example, a media guidance application with PF mode and IMES capabilities may periodically download a database (e.g. located in storage 308 (FIG. 3)) with multiple user attempted or "thought" motions and corresponding EEG signatures. For example, a media guidance application in PF mode detecting a new IMES device corresponding to an arm prosthetic may automatically download from a remote server, and store (e.g. in storage 308 (FIG. 3)) a database of EEG signatures or brain wave patterns specifically associated with arm motions and/or thoughts related to arm motions. Alternatively, a media guidance application system detecting a new user and/or new IMES device may require the user to load a database of associated brain signatures and corresponding intended motions or thoughts. For example, a user may load a database through a user interface (e.g. user input interface 310 (FIG. 3)) and/or removable media or media guidance application elements (e.g. user devices 404 and 406 (FIG. 4)), such as a commercially sold USB drive or SD card. At step 604, during cross-referencing the stored first database may be accessed to determine whether the received EMG signature is present in the first database. For example a commonly used motion for a user with a missing index may be a left to right scrolling motion (e.g. as shown by indicator 132 in display 100 (FIG. 1)). Accordingly, this left to right scrolling motion may be reasonably found in a standard database associated with a missing index, missing fingers, or even missing hand. Alternatively, a different motion may be less common, or may be specific to a user. For example, a user with a missing index finger (e.g. phantom finger 507 (FIG. 5)) may wish to define a double-tap motion. Alternatively, a user with a missing index finger (e.g. phantom finger 507 (FIG. 5)) may wish to define a motion typically associated with a thumb, and accordingly typically listed in a thumb specific database, but not in an index specific database. In the event that the user attempted and/or thought motion is not found, the database may be updated as described above. In the event that the user attempted and/or though motion is found in the first database, the media guidance application may proceed to step 606.

At step 606, the media guidance application (e.g. processing circuitry 306 (FIG. 3)) cross-references the attempted user motion that corresponds to the user EMG signature with a second database (e.g. located in storage 308 (FIG. 3) and updated through a communications network 414 (FIG. 4)) listing media guidance application operations, to determine a media guidance application operation that corresponds to the attempted user motion. For example a user with a missing finger may carry out a left to right scrolling motion, as detected by the cross-referencing in the first database at step 604. At step 606, a second database listing motions and corresponding media guidance application operations is searched for the user's left to right scrolling motion. For example, a left to right scrolling motion may be a common pre-defined motion associated with scrolling through channels. Alternatively, the user motion may be recognized in the first database, but may not be associated with any media guidance application operations in the second database. In some examples, a second database may be specific to a user equipment, and/or a user's media service provider. In the event that the user motion is not associated with a media guidance application operation, the second database may be updated by automatically accessing a remote server, and/or by a manual user update. Alternatively, the user may define a media guide operation associated with the detected user motion, thereby progressively building a customized database of motions and corresponding operations. In some examples, user-defined motions and/or operations may be indicated as private by a user. Alternatively, a user may choose to share user-defined motions and/or operations with a selected group of recipients, and/or to make the user-defined motions and/or operations publicly available. For example, a user may define an intended triple-tap motion of a missing index finger to correspond to a "next channel" command. Another user wishing to assign a media guidance system operation to an intended index triple-tap may then be able to access this previously defined operation when the second database performs an automatic update, which includes other user's defined operations.

At step 608, in response to determining the media guidance application operation to be performed, the media guidance application performs the media guidance application operation on the user device (e.g. for example by scrolling through the grid of channel indicators 102 on display 100 (FIG. 1) or display 312 (FIG. 3)). For example, once a media guidance application operation has been identified, e.g. the user-defined "next channel" operation corresponding to a triple-tap motion, or the standard scrolling through program listings associated with a left to right motion, the media guidance application implements the operation, e.g. the scrolling or next channel.

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one of more of the steps in FIG. 6.

Figure 7:
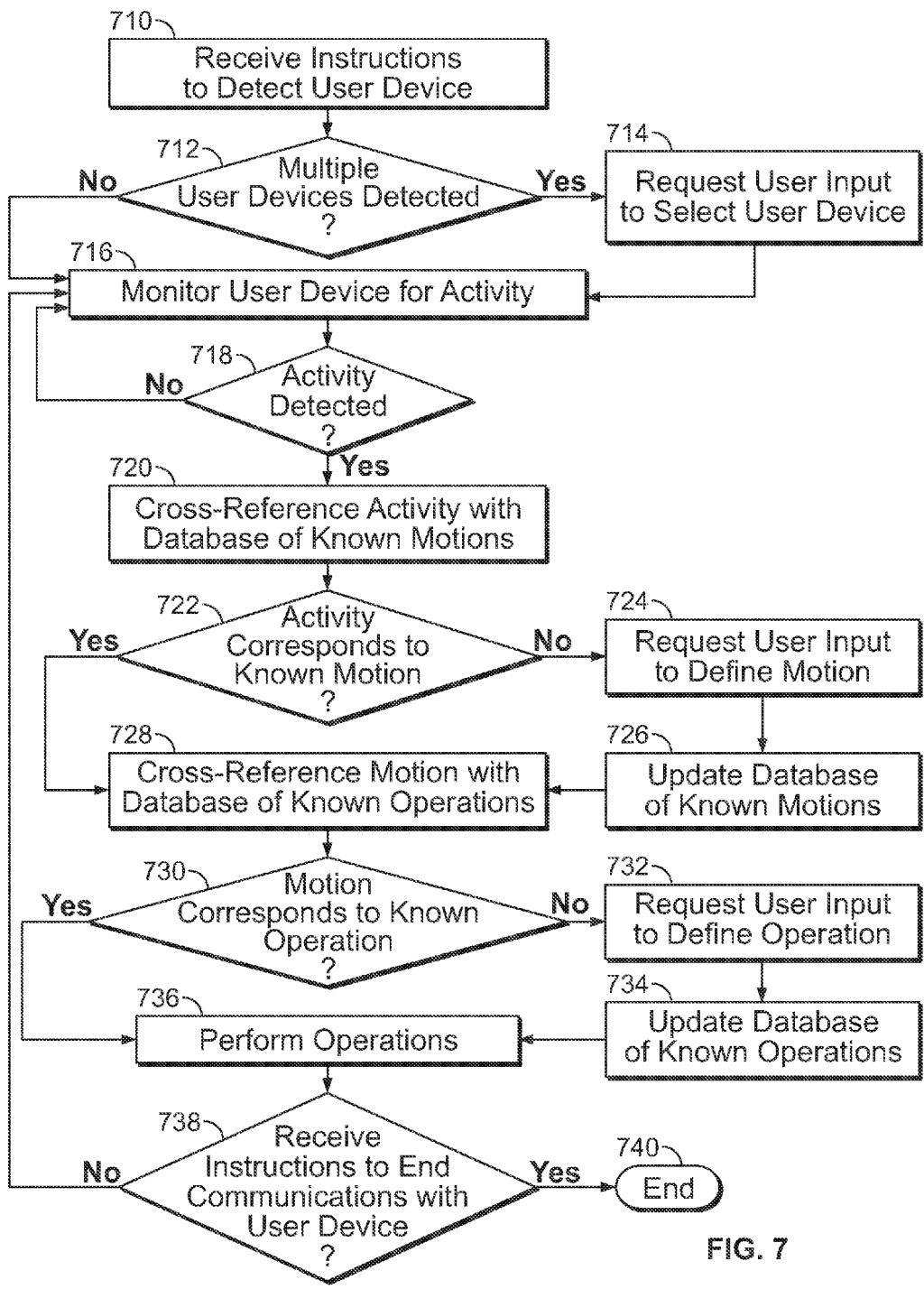
FIG. 7 is a flow-chart of illustrative steps involved in performing a media guidance application operation based on a user intended motion, in accordance with some embodiments of the disclosure.

FIG. 7 is a flow-chart of illustrative steps involved in performing a media guidance application operation based on a user intended motion (e.g. a swiping motion as represented by indicator 132 (FIG. 1), in accordance with some embodiments of the disclosure.

At step 710, the media guidance application may receive instructions to detect a user device (e.g. an IMES component 316 (FIG. 3) or 506 (FIG. 5)). For example, a first user with a missing arm, fitted with an IMES device and corresponding arm prosthetic typically controlled by the IMES device when the arm prosthetic is worn, may wish to control the media guidance application to tune in to the evening news. In some examples, the user may turn on a "PF" mode by turning on his IMES device, where the media guidance application system is continuously scanning for new IMES devices. Alternatively, a user may turn on a "PF" mode by selecting selectable option 204 (FIG. 2)), thereby actively requesting that the media guidance application scan and detect for available, powered, IMES devices.

At step 712, the media guidance application (e.g. processing circuitry 306 (FIG. 3) determines whether multiple user devices (e.g. user television equipment 402, user computer equipment 404, and/or wireless user communications device 406 (FIG. 4)) are detected. At step 712, in particular, processing circuitry 306 determines whether multiple user devices such as multiple IMES components 316 (FIG. 3) or 506 (FIG. 5) are detected. For example, media guidance application may scan for RF signals to identify the existence of multiple sources of RF signals. In this example, media guidance application may first scan for alternative signals or device indicators, then determine whether a device emitting an RF signal is an IMES device. For example, within a home there may be several IMES devices associated with prosthetics capable of emitting RF signals, but there may also be several other devices capable of emitting RF signals. In this example, the media guidance application may detect all devices capable of emitting RF signals, and select from these devices those which may be identified as IMES-type devices, which may be one or more. In the event that multiple user devices (e.g. IMES component 316, (FIG. 3)) indicating users with prosthetic capabilities are detected, the media guidance application may proceed to step 714, to request user input in selecting a user device (e.g. IMES component 316 (FIG. 3)). For example, a user may have multiple prosthetics, or there may be multiple users with prosthetics operating the media guidance application. In these embodiments, processing circuitry 306 may determine which user associated with which prosthetic (and which corresponding phantom limb) to monitor for RF signals. Furthermore, databases accessed to determine intended motions and corresponding media guidance operations (e.g. located in storage 308) may vary depending on the user and/or associated prosthetic. For example, Tom, missing a right hand, may access a stored database which is different than the database accessed when Suzy is operating the media guidance application, since Suzy is missing a left hand. In these examples, the media guidance application may have a default prosthetic setting, and/or may require, as in step 714, user input to determine which IMES device to monitor for RF signals (e.g. through user input interface 310 (FIG. 3)).

In the event that multiple devices are not detected, the media guidance application may proceed to step 716, to monitor the identified user device, e.g. an IMES component 316 or 506, for activity such as RF signals. For example, a user may choose to activate PF mode when getting home from work, and proceed to cook dinner. In this example, the user's identified IMES device may be monitored as soon as the PF mode is activated, such that when the user desires to switch channels to the news at 8 pm, or when the user wishes to switch to VOD before dessert, the media guidance application which has been monitoring the IMES device can immediately detect the user's IMES device actively emitting an RF signal. In some example, the media guidance application monitoring the IMES device may be monitoring for a meaningful EEG signature. EEG signatures and radio signals may be voluntarily or involuntarily created while the user is preparing his dinner, but the EEG signature and/or radio signals may have characteristics which are not indicative of a meaningful transmission. In other words, some detected RF signals may be qualified as "noise" and ignored by the media guidance application, until a meaningful, i.e. meeting certain specific characteristics in length, strength, etc. is detected.

In the event that activity is detected from the user device, at step 718, the media guidance application may proceed to step 720, at which the media guidance application cross-references the detected activity, e.g. RF signal, and/or corresponding EEG signature, and cross-references the activity pattern e.g. the EEG signature with an appropriate database of known motions (e.g. stored in storage 308 (FIG. 3)). As noted above, the appropriate database may depend on the user, and/or phantom limb the user intends to move. Furthermore, the databases may be updated by users, and/or by external sources (e.g. through communications network 414, (FIG. 4)) such as a web server, or satellite link. For example, for Marc, a user with a missing hand, the media guidance application may access a database specific to EEG signatures corresponding to hand motions. In addition, over time the media guidance application system may, based on Marc's specific inputs (e.g. discrete motions) and/or general input characteristics (e.g. strength and length of EEG patterns) build a database of EEG signatures and corresponding motions which is specific to Marc, and may contain more EEG patterns than a standard missing hand database, and/or different EEG patterns.

At step 722, the media guidance application may determine whether the brain activity, e.g. the identified EEG signature corresponds to a known motion. For example, an EEG signature may be detected in the "baseline" database as corresponding to an index finger's left to right motion. Alternatively, the EEG signature or brain activity may be detected as corresponding to the left to right motion after steps 724 and 726 have been carried out, e.g. after Marc has defined a user specific EEG signature-intended motion pair.

As noted above, when no known motion is found corresponding to the identified EEG signature, the media guidance application (e.g. processing circuitry 306 (FIG. 3)) proceeds to step 724 at which a user input may be requested to define the user motion. For example, a user may input text, and/or select a combination of keys through a user input interface (e.g. user input interface 310, (FIG. 3). For example, user Marc with a missing hand may provide a one time indication to the system that an EEG signature corresponds to a left to right motion. For example, when no motion is detected, the media guidance application system may prompt Marc to use a pointer or mouse to carry out the motion on the media guidance application display. Alternatively, the media guidance application may also provide a list of potential user motions, based on data from other users, and/or based on motions which had EEG signatures close to, but not identical to, the EEG signature created by the user. Alternatively, the media guidance application system may determine a sensitivity issue and may initiate a recalibration of the telemetry controller, and/or user IMES sensors.

At step 726 a database (e.g. stored in storage 308 (FIG. 3)) of known motions associated with EEG signatures is updated to reflect the input provided by the user at step 724. For example, the database may be updated to include Marc's previously described triple tap index motion as corresponding to the EEG signature Marc generated, and which was received and processed by the IMES device (e.g. IMES component 316 (FIG. 3)). As noted above, the media guidance application system may further automatically upload the user-defined motion to a server for access by other users at other media guidance application systems. Alternatively, the media guidance application system may prompt the user to select whether the EEG pattern and user-defined motion association will be private or shared with one or more other users.

Once an activity has been identified as corresponding to a known motion, or associated with a newly stored known motion, the media guidance application (e.g. processing circuitry 306 (FIG. 3)) proceeds to step 728 where the known motion is cross-referenced with a database of known operations.

As noted above, the appropriate database listing intended motions and corresponding operations may depend on the user, and/or media guide provider. Furthermore, the databases may be updated by users, and/or by external sources (e.g. through communications network 414, (FIG. 4)) such as a web server, or satellite link. For example, for Marc, a user with a particular media guidance application system and/or media provider, and/or subscription package, the media guidance application may access a database specific to these characteristics. In addition, over time the media guidance application system may, based on Marc's specific inputs (e.g. assigning operations to previously known motions, or assigning operations to new motions) build a database of motions and corresponding operations which is specific to Marc, and may contain more operations than a standard out of the box database, and/or different operations associated with common motions, reflecting the user's preferred motions and most frequently used operations.

At step 730, the media guidance application determines whether the identified motion corresponds to a known operation. For example, the triple-tap of the index finger defined by a user at step 724 may not have been assigned a corresponding media guidance system operation yet. In another example, a motion may have been assigned to an operation, but a user may wish to assign a different operation to the motion. For example, Marc may wish to assign a "switch to VOD" operation to a left to right scrolling motion, whereas the standard database would typically associate a left to right scrolling motion with a "switch to next channel" operation.

In the event that the motion does not correspond to a known operation, or in the event that the user indicates a desire to reassign the motion to a new and/or different operation, the media guidance application proceeds to step 732, and may request user input to define the media guidance application operation correspond to the user intended motion identified at step 730. For example, similarly to step 724, the user may input text, and/or select from a menu, and/or select a combination of keys through a user input interface (e.g. user input interface 310, (FIG. 3)) to define an operation associated with the intended motion detected at step 722. In this example, the media guidance application may provide a user with an option to start, record a sequence of keys and operations performed on the media guidance application via conventional means, and end. In Marc's example, Marc may "record" a sequence of keys and navigation commands using his able hand, and/or prosthetic, and/or voice command to switch to VOD.

The media guidance application, at step 734, may then accordingly update the database (e.g. stored in storage 308 (FIG. 3)) associating known motions with corresponding known media guidance application operations. In the example described above, the recorded sequence will be assigned by the media guidance application to the previously determined user motion, e.g. the left to right scrolling motion in this case.

Once the user intended motion has been associated with a media guidance application operation, the media guidance application may proceed to step 736 at which the media guidance application operation is performed (e.g. on display 312 (FIG. 3), as shown e.g. in illustrative grid program listings displays 100 and 200 (FIGS. 1 and 2)). If the media guidance application receives instructions to end communications with the user device, e.g. the IMES device or its sub-components, the interaction ends at step 740. For example, a user may instruct the media guidance application to exit the prosthetic free "PF" mode, and/or may turn off their IMES device (e.g. when going to sleep), and/or may instruct the media guidance application of a switch between device users, e.g. switching users (e.g. between Tom and Suzy) or switching the IMES device used (e.g. Mary is now intending motion in her missing left hand, rather than previously intending motion in her missing right hand). If no instructions to end the communications are received (e.g. by processing circuitry 306 (FIG. 3)) at step 738, the media guidance application may continue to monitor the IMES device for user activity at step 716.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one of more of the steps in FIG. 7.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real-time. It should also be noted, the systems and/or methods described above may be applied to, or used in accordance with, other systems and/or methods.

What is claimed is:

1. A method for controlling a user device, the method comprising:
   receiving an RF signal from a user device, wherein the RF signal corresponds to an electromyography (EMG) signature received from a user;
   comparing the EMG signature with a first database listing EMG signatures that corresponds to different attempted user motions to determine an attempted user motion that corresponds to the user EMG signature;
   comparing the attempted user motion that corresponds to the user EMG signature with a second database listing media guidance application operations to determine a media guidance application operation that corresponds to the attempted user motion; and
   in response to determining the media guidance application operation to be performed, performing the media guidance application operation on the user device,
      wherein the attempted user motion relates to motion of an appendage that is no longer attached to the user, and
      wherein the media guidance application operation provides media guidance data to the user.

2. The method of claim 1, wherein the receiving the RF signal from the user device further comprises:
   receiving the EMG signature from the user at a telemetry controller; and
   processing the EMG signature at the telemetry controller into the received RF signal.

3. The method of claim 2, further comprising:
   in response to not determining an attempted user motion corresponding to the EMG signature, recalibrating the telemetry controller.

4. The method of claim 2, further comprising:
   in response to not determining a media guidance application operation corresponding to the attempted user motion, recalibrating the telemetry controller.

5. The method of claim 1, further comprising:
   in response to not determining an attempted user motion corresponding to the EMG signature, prompting the user to enter the attempted user motion by a different method; and updating the first database.

6. The method of claim 1, further comprising:
   in response to not determining an attempted user motion corresponding to the EMG signature, searching for an attempted user motion from a different source.

7. The method of claim 1, further comprising:
   in response to not determining the media guidance application operation that corresponds to the attempted user motion, prompting the user to enter the media guidance application operation by a different method; and updating the second database.

8. The method of claim 1, further comprising:
   in response to not determining the media guidance application operation that corresponds to the attempted user motion, generating for display to the user a media guidance application operation which resembles the attempted user motion.

9. The method of claim 1, further comprising:
   in response to not determining the media guidance application operation that corresponds to the attempted user motion, searching for an attempted user motion from a different source.

10. A system for controlling a user device, the system comprising:
    stored circuitry configured to:
       store a first database listing electromyography (EMG) signatures that correspond to different attempted user motions, and
       store a second database listing media guidance application operations that correspond to attempted user motions; and control circuitry configured to:
       receive an RF signal from a user device, wherein the RF signal corresponds to an EMG signature received from a user;

compare the EMG signature with the first database to determine an attempted user motion that corresponds to the user EMG signature;

compare the attempted user motion that corresponds to the user EMG signature with the second database to determine a media guidance application operation that corresponds to the attempted user motion; and in response to determining the media guidance application operation to be performed, perform the media guidance application operation on the user device, wherein the attempted user motion relates to motion of an appendage that is no longer attached to the user, and wherein the media guidance application operation provides media guidance data to the user.

11. The system of claim 10, wherein the control circuitry configured to receive the RF signal from the user device is further configured to:

receive the EMG signature from the user at a telemetry controller; and process the EMG signature at the telemetry controller into the received RF signal.

12. The system of claim 11, the control circuitry further configured to:

in response to not determining an attempted user motion corresponding to the EMG signature, recalibrate the telemetry controller.

13. The system of claim 11, the control circuitry further configured to:

in response to not determining a media guidance application operation corresponding to the attempted user motion, recalibrate the telemetry controller.

14. The system of claim 10, the control circuitry further configured to:

in response to not determining an attempted user motion corresponding to the EMG signature, prompt the user to enter the attempted user motion by a different method; and update the first database.

15. The system of claim 10, the control circuitry further configured to:

in response to not determining an attempted user motion corresponding to the EMG signature, search for an attempted user motion from a different source.

16. The system of claim 10, the control circuitry further configured to:

in response to not determining the media guidance application operation that corresponds to the attempted user motion, prompt the user to enter the media guidance application operation by a different method; and update the second database.

17. The system of claim 10, the control circuitry further configured to:

in response to not determining the media guidance application operation that corresponds to the attempted user motion, generate for display to the user a media guidance application operation which resembles the attempted user motion.

18. The system of claim 10, the control circuitry further configured to:

in response to not determining the media guidance application operation that corresponds to the attempted user motion, search for an attempted user motion from a different source.

\* \* \* \* \*